(12) United States Patent
Mupende et al.

(10) Patent No.: US 10,011,464 B2
(45) Date of Patent: Jul. 3, 2018

(54) APPARATUS FOR RECOGNIZING THE DISCARD STATE OF A HIGH-STRENGTH FIBER ROPE IN USE IN LIFTING GEAR

(71) Applicant: LIEBHERR-COMPONENTS BIBERACH GMBH, Biberach an der Riss (DE)

(72) Inventors: Ilaka Mupende, Neu-Ulm (DE); Horst Zerza, Biberach (DE)

(73) Assignee: Liebherr-Components Biberach GMBH, Biberach an der Riss (DE)

( * ) Notice: Subject to any disclaimer, the term of this patent is extended or adjusted under 35 U.S.C. 154(b) by 0 days.

(21) Appl. No.: 15/139,236

(22) Filed: Apr. 26, 2016

(65) Prior Publication Data

US 2016/0236913 A1     Aug. 18, 2016

Related U.S. Application Data

(63) Continuation of application No. 13/950,204, filed on Jul. 24, 2013, now Pat. No. 9,335,318, which is a
(Continued)

(30) Foreign Application Priority Data

Jan. 24, 2011    (DE) .................... 20 2011 001 846 U

(51) Int. Cl.
     *B66C 13/16*        (2006.01)
     *G01N 3/08*         (2006.01)
     (Continued)

(52) U.S. Cl.
     CPC .............. *B66C 13/16* (2013.01); *B66C 13/18* (2013.01); *B66C 15/00* (2013.01); *B66C 15/06* (2013.01);
(Continued)

(58) Field of Classification Search
None
See application file for complete search history.

(56) References Cited

U.S. PATENT DOCUMENTS 3,916,686 A * 11/1975 Lear .................... G01M 99/007
                                                                   374/49
4,022,010 A * 5/1977 Gladenbeck ........... D07B 1/025
                                                                   57/231
(Continued)

FOREIGN PATENT DOCUMENTS

CN             2154484        1/1994
CN             1134484        10/1996
(Continued)

*Primary Examiner* — Quan-Zhen Wang
*Assistant Examiner* — Chico A Foxx
(74) *Attorney, Agent, or Firm* — Levine Bagade Han LLP

(57) ABSTRACT

The present invention relates generally to lifting gear such as cranes which use high-strength fiber ropes instead of steel ropes. In this respect, the invention in particular relates to an apparatus for recognizing the discard state of a high-strength fiber rope in use at such lifting gear comprising a detection device for detecting at least one rope parameter as well as comprising an evaluation unit for evaluating the rope parameter and for providing a discard signal in dependence on the rope parameter evaluation. In accordance with the invention, the detection device of the apparatus for recognizing the discard state comprises a plurality of differently configured detection means for a magnetic, mechanical, optical and/or electronic detection of a plurality of different rope parameters which can be evaluated by the evaluation unit individually and/or in combination with one another for recognizing the discard state.

13 Claims, 5 Drawing Sheets

Related U.S. Application Data continuation of application No. PCT/EP2012/000311, filed on Jan. 24, 2012.

(51) Int. Cl.
| | | |
|---|---|---|
| *B66C 13/18* | (2006.01) | |
| *B66C 15/00* | (2006.01) | |
| *B66D 1/54* | (2006.01) | |
| *G01N 3/14* | (2006.01) | |
| *B66C 15/06* | (2006.01) | |
| *G01N 33/36* | (2006.01) | |

(52) U.S. Cl.
CPC ............... *B66D 1/54* (2013.01); *G01N 3/08* (2013.01); *G01N 3/14* (2013.01); *G01N 33/36* (2013.01)

(56) References Cited

U.S. PATENT DOCUMENTS

| | | | | |
|---|---|---|---|---|
| 4,750,430 A | * | 6/1988 | Morton | B63B 27/18 104/114 |
| 5,645,181 A | * | 7/1997 | Ichiba | B66C 13/46 212/281 |
| 5,834,942 A | | 11/1998 | De Angelis | |
| 5,890,564 A | * | 4/1999 | Olsen | B66B 7/123 187/250 |
| 6,123,176 A | * | 9/2000 | O'Donnell | B66B 7/10 187/393 |
| 6,247,359 B1 | * | 6/2001 | De Angelis | D07B 1/14 73/158 |
| 7,117,981 B2 | | 10/2006 | Logan | |
| 7,134,645 B1 | * | 11/2006 | Johnson | B66D 1/741 254/338 |
| RE40,166 E | | 3/2008 | Sukhorukov et al. | |
| 2003/0052695 A1 | | 3/2003 | Smith | |
| 2003/0089551 A1 | * | 5/2003 | Kato | B66B 7/06 182/1 |
| 2003/0111298 A1 | * | 6/2003 | Logan | B66B 7/1238 187/391 |
| 2004/0026178 A1 | * | 2/2004 | Honda | B66B 7/06 187/251 |
| 2004/0099062 A1 | * | 5/2004 | Smith | B66B 7/1215 73/801 |
| 2005/0060979 A1 | * | 3/2005 | Aulanko | B66B 11/08 57/232 |
| 2005/0192732 A1 | | 9/2005 | Narisawa et al. | |
| 2005/0226584 A1 | * | 10/2005 | Williams | D04C 1/02 385/130 |
| 2006/0243537 A1 | * | 11/2006 | Finn | D07B 1/148 187/394 |
| 2007/0089938 A1 | * | 4/2007 | Ishioka | B66B 7/08 187/391 |
| 2007/0205405 A1 | * | 9/2007 | Stockmaster | B66D 3/18 254/275 |
| 2009/0320436 A1 | * | 12/2009 | Kirth | D02J 1/22 57/255 |
| 2011/0089130 A1 | * | 4/2011 | Stephan | B66C 1/12 212/262 |
| 2011/0172932 A1 | | 7/2011 | Bachmann et al. | |
| 2012/0053852 A1 | | 3/2012 | Padilla et al. | |
| 2012/0120389 A1 | | 5/2012 | Logan et al. | |
| 2013/0119256 A1 | | 5/2013 | Husmann et al. | |
| 2013/0247534 A1 | * | 9/2013 | Canedo Duarte da Rocha | D07B 1/0613 57/220 |
| 2014/0027401 A1 | | 1/2014 | Ilaka et al. | |
| 2014/0305744 A1 | | 10/2014 | Kere et al. | |
| 2014/0311323 A1 | * | 10/2014 | Erlendsson | D07B 1/025 87/6 |
| 2016/0221800 A1 | * | 8/2016 | Mupende | G01N 3/22 |

FOREIGN PATENT DOCUMENTS

| | | |
|---|---|---|
| CN | 1433372 | 7/2003 |
| CN | 101195969 | 6/2008 |
| DE | 19956265 | 6/2005 |
| EP | 0749934 | 12/1996 |
| EP | 0845672 | 6/1998 |
| EP | 1930496 | 6/2008 |
| JP | 56-064603 | 6/1981 |
| JP | 60-253810 | 12/1985 |
| JP | 1995-181167 | 7/1995 |
| JP | 1997-188496 | 1/1997 |
| JP | 9012271 | 1/1997 |
| JP | 9188496 | 7/1997 |
| JP | 40-9278381 | 10/1997 |
| JP | 1998-019549 | 1/1998 |
| JP | 1998-182036 | 7/1998 |
| JP | 10318741 | 12/1998 |
| JP | 411352050 | 12/1999 |
| JP | 2000-170082 | 6/2000 |
| JP | 2000-327272 | 11/2000 |
| JP | 2000327272 | 11/2000 |
| JP | 2000327272 A * | 11/2000 |
| JP | 2001192183 | 7/2001 |
| JP | 20013-02135 | 10/2001 |
| JP | 2001302135 | 10/2001 |
| JP | 2002333431 | 11/2002 |
| JP | 2005134261 | 5/2005 |
| JP | 2005189157 | 7/2005 |
| JP | 2006097398 | 4/2006 |
| JP | 2010-149980 | 7/2010 |
| WO | WO 2007/062357 | 5/2007 |

* cited by examiner

APPARATUS FOR RECOGNIZING THE DISCARD STATE OF A HIGH-STRENGTH FIBER ROPE IN USE IN LIFTING GEAR

CROSS-REFERENCE TO RELATED APPLICATIONS

This application is a continuation of U.S. patent application Ser. No. 13/950,204 filed on Jul. 24, 2013, which is a continuation of PCT Application No. PCT/EP2012/000311, filed on Jan. 24, 2012, which claims priority to German Patent Application No. 20 2011 001 846.6, filed on Jan. 24, 2011, all of which are incorporated herein in their entireties.

BACKGROUND

1. Technical Field

The present invention relates generally to lifting gear such as cranes which use high-strength fiber ropes instead of steel ropes. In this respect, the invention in particular relates to an apparatus for recognizing the discard state of a high-strength fiber rope in use at such lifting gear comprising a detection device for detecting at least one rope parameter as well as comprising an evaluation unit for evaluating the rope parameter and for providing a discard signal in dependence on the rope parameter evaluation.

2. Description of Related Art

In recent times, trials have been made with cranes to use high-strength fiber ropes made from synthetic fibers such as aramid fibers (HPMA), aramid/carbon fiber mixtures, high-modulus polyethylene fibers (HMPE) or poly(p-phenylene-2,6-benzobisoxazole) fibers (PBO) instead of the proven steel ropes used for many years. The advantage of such high-strength fiber ropes is their low weight. Such high-strength fiber ropes are considerably lighter than corresponding steel ropes at the same rope diameters and the same or higher tensile strength. In particular with high cranes with correspondingly large rope lengths, a greater weight saving is hereby achieved which enters into the dead-weight load of the crane and results in correspondingly higher payloads with an otherwise unchanged construction design of the crane.

A disadvantageous property of such high-strength fiber ropes is, however, their break behavior or their failure without substantial, longer preliminary signs. Whereas the wear is clearly visible in steel ropes and signals a failure over a longer period in advance, for example by the breakage of individual steel wires and a corresponding splaying which is easily noticed, high-strength fiber ropes show hardly any signs of excessive wear which would be easily perceivable for the eye and which would show themselves clearly over a longer period before the actual failure. In this respect, intelligent monitoring measures are required to recognize the discard state of high-strength fiber ropes in time.

An apparatus is known from DE 199 56 265 B4 for monitoring the operation of hoist winches on cranes which monitors the rope force of the hoist rope and the lever arm of the hoist rope on the rope winch and determines therefrom the load applications acting on the rope winch which are stored in a load spectrum counter. This load spectrum counter is integrated into the hoist winch to maintain the history of the hoist winch retraceably on a removal and reinstallation of the hoist winch. A load spectrum counter is furthermore known from EP 0 749 934 A2 which determines the load changes which occur, determines the rope force acting on the hoist winch at each load change, calculates the load spectrum therefrom and calculates and displays the remaining service life of the hoist winch while considering the so-called Wöhler curves.

Such monitoring measures of the hoist winch can, however, not really reliably give the remaining service life or the discard state of a high-strength fiber rope since the high-strength fiber ropes are subject to a variety of strains and impairments which influence the wear and which are independent of the winch strain, for instance e.g. the deflection and bending strains at pulley blocks, external blows and buffets on the rope, surface contamination of components contacting the rope, etc. On the other hand, inflexible service life standards for high-strength fiber ropes are practically incompatible with respect to economic utilization of the actual service life and observation of the required safety since the service life and wear of the high-strength fiber rope can fluctuate strongly in dependence on the conditions of use and on the external influences on the high-strength fiber rope.

SUMMARY OF THE INVENTION

Starting from this, it is the underlying object of the present invention to provide an improved apparatus for determining the discard state of high-strength fiber ropes which avoids disadvantages of the prior art and further develops the latter in an advantageous manner. A reliable, precise determination of the discard state should preferably be achieved which economically utilizes the remaining service life of the fiber rope without putting safety at risk and manages for this purpose with simple detection devices which also operate reliably under difficult conditions of use for construction machinery.

This object is achieved in accordance with the invention by an apparatus in accordance with claim 1. Preferred embodiments of the invention are the subject of the dependent claims.

In accordance with an advantageous aspect of the present invention, it is therefore proposed not to rely on a single criterion in the determination of the discard state, but rather to avoid the problems of the advance signs which can only be detected with difficulty in that different relevant parameters of the fiber rope are monitored for changes and the discard state is determined on a greater change of an individual parameter or on a plurality of smaller changes of a plurality of parameters. In accordance with the invention, the detection device of the apparatus for recognizing the discard state comprises a plurality of differently configured detection means for a magnetic, mechanical, optical and/or electronic detection of a plurality of different rope parameters which can be evaluated by the evaluation unit individually and/or in combination with one another for recognizing the discard state. The use of different rope parameters such as the named transverse compressive stiffness and cross-sectional change or, alternatively or additionally thereto, a rope lengthening and magnetic rope properties or other mechanical, optical and/or electronic rope parameters for the determination of the discard state is based on the consideration that depending on the strain and on the effects on the fiber rope it may from case to case be a different parameter which displays the rope wear or signals the discard state or the discard state may also not display itself by an actually larger change of only a single parameter, but rather by smaller changes of a plurality of parameters.

In a further development of the invention, the named evaluation unit is configured such that a discard signal is provided when at least one of the detected rope parameters or its change exceeds/falls below an associated limit value and also when an indirect rope parameter or its change derived from all detected rope parameters or from a subgroup of the detected rope parameters exceeds/falls below an associated limit value.

In a further development of the invention, the named evaluation unit is configured such that not only a plurality of rope parameters per se are detected and examined for respective changes or are compared with limit values, but also dependencies between the plurality of rope parameters are taken into account. For example, permitted changes and/or permitted limit values for a rope parameter can be shifted or changed when a different rope parameter has undergone a predefined change. In particular more complex phenomena of fatigue or damage can hereby be detected and the discard state recognized. If it is, for example, assumed that an increase in the transverse compressive stiffness is accompanied by a decrease in the rope diameter, the limit value for the rope diameter can be lowered and/or the desired range for the permitted rope diameter can be decreased on the detection of an increased transverse compressive stiffness by the evaluation unit. If the measurement then determines that the rope diameter fills below the lowered rope diameter limit value and/or drops out of the reduced desired range, a discard signal can be output. In a similar manner, alternatively or additionally hereto, further dependencies between the most varied rope parameters can be taken into account by the evaluation unit, for example the aforesaid dependency between the rope stiffness and the rope lengthening, for example such that, on a higher bending stiffness, an increasing rope length is expected and is taken into account by corresponding limit values.

In this respect, in a further development of the invention, different rope parameters can be used. In accordance with a further aspect of the present invention, it is proposed to monitor a change in the transverse compressive stiffness or in the rope cross-section and to use it as an indicator for the discard state. The detection device for detecting rope changes can in particular have transverse compressive stiffness determination means and/or cross-sectional determination means for determining the transverse compressive stiffness or the rope cross-section, wherein the evaluation unit monitors the transverse compressive stiffness or the determined rope cross-section for changes and provides a discard signal as necessary.

It can be shown in long-term tests of high-strength fiber ropes that as the strain and the number of bending cycles increase, the transverse compressive stiffness changes in a characteristic manner, in particular shows an increase. The degree of changing transverse compressive stiffness can therefore also be used in an advantageous manner for fixing the time of the discard. In this respect, an increase in the transverse compressive stiffness can be accompanied by a reduction in the rope diameter. The rope can be given a higher bending stiffness and/or a permanent, measurable rope lengthening can take place. A dependence of the change of the transverse compressive stillness on the change of the rope diameter can in particular be detected, wherein in particular an increase in the transverse compressive stiffness can be detected in dependence on a rope diameter reducing in size. Alternatively or additionally, a dependency of the change of the rope stiffness on the change in the rope length can be determined, wherein in particular an increase in the rope stiffness in dependence on an increase in the rope length can be determined. The output of the discard signal can in this respect generally take place in dependence on the monitored transverse compressive stiffness or on the rope cross-section. However, a more precise determination of the discard state can advantageously take place by the taking into account of the different rope parameters.

The transverse compressive stiffness of the rope can in this respect generally be determined in various manners. In an advantageous further development of the invention, the calculated data from the drum diameter, rope diameter, rope specification and tensile force can be used as the basis for the measurement or the measurement process can be controlled in dependence on the named calculated data from the drum diameter, rope diameter, rope specification and tensile force and the corresponding measurement parameters can be set. The transverse compressive stiffness can in particular be carried out while acting on the rope with a predefined tensile load, wherein the predefined tensile load can advantageously be selected in the range of actually occurring tensile loads in the operation of the lifting gear in accordance with its intended use. Phenomena of damage or fatigue of the rope can be determined better by the determination of the transverse compressive stiffness under a tensile load of the rope.

In a further development of the invention, one rope portion or a plurality of rope portions can be acted on by a respective predefined transverse force, can in particular be clamped, for determining the transverse compressive stiffness, wherein the change in the diameter and/or the change in the cross-section of the rope is/are detected or determined which is/are adopted under the transverse force. In this respect, with a predefined transverse force, the change in cross-section or diameter which is adopted can be measured and/or alternatively the transverse force required for achieving a predefined change in cross-section and/or diameter can be measured. Alternatively or additionally, varying transverse forces can be applied and the change in cross-section or diameter adopted in dependence on the varying transverse force can be determined and/or alternatively the transverse forces required for the achieving of different changes in cross-section or diameter can be measured.

In an advantageous further development of the invention, the rope can be introduced for determining its transverse compressive stiffness between two mutually oppositely disposed clamping jaws which can advantageously each have a rope groove and can be clamped by the clamping jaws in that they are moved toward one another by a suitable adjustment apparatus.

In this respect, the rope cross-section can generally be detected in different manners. Advantageously, the named rope cross-section determination means can comprise diameter detection means for detecting the rope diameter in at least two different planes and determine the rope cross-sectional area from the named two determined rope diameters. Such a detection of a rope portion or of a plurality of rope portions in a plurality of planes can also be provided in the aforesaid determination of the transverse compressive stiffness, for example such that the respective rope portion is clamped, simultaneously or sequentially by a plurality of clamping jaw pairs which are positioned associated with one another in different planes. It would admittedly generally also be conceivable to determine or derive the rope cross-sectional area from only one rope diameter which was determined in one plane. Advantageously, however, the rope cross-section or the rope cross-sectional area is determined from two rope diameters which were determined in different planes standing approximately perpendicular to one another since hereby changes and/or deformations in cross-section unharmful for the strength of the fiber rope can be taken into account and premature wear assumptions can be avoided.

High-strength fiber ropes show ovalizing cross-sectional changes under transverse loads such as can occur, for example, at rope rollers or at the rope winch, i.e. the cross-section which is circular per se in the starting state is changed toward a section pressed flat, which is per se not yet harmful for the durability or strength of the fiber rope. If, however, the rope cross-section changes such that the cross-sectional area reduces, this is advantageously considered as a sign for incipient wear. The evaluation device can in particular provide a discard signal when the rope cross-section shows a predefined tapering or if a reduction in size of the rope cross-sectional area exceeds a predefined measure.

The diameter determination can in this respect take place in different manners. For example, an optical sampling by means of light radiation and an associated sensor for detecting the shadow width could be provided. In an advantageous further development of the invention, however, a mechanical sampling of the rope takes place from oppositely disposed sides to determine the rope diameter. At least one elastically preloadable clamping means pair can preferably be provided, preferably in the form of rope rollers which can be pressed against the rope or clamping jaws having rope grooves with which a distance measurement unit is associated to measure the distance of the clamping means from one another in the state applied to the rope.

In an advantageous further development of the invention, the transverse compressive stiffness determination and the rope cross-section determination or diameter determination can be carried out by the same clamping means pair or by the same clamping means pairs so that measuring times can be saved and different clamps can be avoided. For example, a pure determination of diameter or cross-section can take place under sufficiently small transverse pressing forces which can then be increased to carry out the measurement of the transverse compressive stiffness.

In order not to impair the diameter determination by deflections of the rope, the named sampling means can be movably suspended so that they can participate in rope movements, in particular transverse rope movements, in the state applied to the rope. The aforesaid preloadable clamping means in the form of rope rollers can in particular be moved relative to one another, on the one hand, and transversely and/or parallel to the longitudinal rope length together, on the other hand, to be able to determine the rope diameter exactly even with unwanted rope deflections.

The rope measurement advantageously takes place in at least two planes to be able to eliminate deviations of the rope cross-section from the circular shape on the determination of the cross-sectional area. For this purpose, for example, two rope roller pairs or clamping jaws can be provided which are arranged in planes perpendicular to one another and can each be elastically clamped against one another.

In a further development of the invention, alternatively or additionally to the named transverse compressive stiffness or cross-sectional area or cross-sectional shape, different other rope parameters can be used in accordance with a further aspect of the present invention, a change of an indicator section which is embedded in the fiber rope and which comprises a different material than the rope fibers is monitored in this respect in an advantageous manner. The change in the fibers or fiber strands of the fiber rope itself, which can only detected with difficulty, can be bypassed by means of such an indicator section which can be embedded in the core of the strand or which can also be arranged between the fiber strands of the fiber rope, in particular when the indicator section is selected with respect to its configuration and/or with respect to its material such that the indicator section shows changes faster than the fiber strands of the fiber rope and/or such changes can be detected more easily. The monitoring of such an indicator section in the fiber rope can in this respect also bring along special advantages only per se without monitoring further parameters.

The indicator section can in particular comprise a material, preferably a metallic continuous section, which influences a magnetic field and/or is magnetically conductive and/or magnetizable. The detection means are in this respect advantageously configured as operating magnetically, wherein in particular a magnetic field sensor can be provided by means of which the magnetic properties of the named indicator section can be determined. The magnetic properties of the indicator section in particular change on a break of the indicator section so that a corresponding change of the magnetic flux or of the magnetic field can be detected easily and can be utilized as a wear indicator. If a break of the magnetically conductive indicator section takes place, it can be recognized by a magnetically inductive monitoring or it can be detected by a corresponding interruption of the magnetic field.

Alternatively or additionally to such a magnetically operating configuration of the indicator section and of the associated detection means, changes in the named indicator section can optionally also be monitored differently and other monitoring principles can also be used. For example, the indicator section can be configured as electrically conductive and the electrical conductivity of the fiber rope or of the indicator section provided therein can be monitored using correspondingly configured detection means. Alternatively or additionally, a thermal conductivity of the named indicator section could also be monitored, wherein here the indicator section is advantageously configured from a material having good thermal conductivity, for example from a silver wire.

The named indicator section which is embedded in the fiber rope and which comprises a different material than the rope fibers is advantageously configured weaker than the fiber rope with respect to its resistance capability toward rope strains, stretch, tension, bending, torsion, UV-radiation, water absorption and/or temperature such that the indicator section fails considerably faster than the fiber rope or its fiber strands. It is hereby ensured that a change in the indicator section can be determined in time before a failure of the fiber rope occurs. A break of the named indicator section does not yet have any real effect on the strength of the fiber rope itself, but can be determined easily and can be detected in time before the occurrence of the failure of the rope.

In a further development of the invention, the detection device monitors in which rope portion a rope change occurs which is used to determine the discard state to be able to identify the worn or damaged rope portion and optionally to be able to continue to use the remaining rope, for example in that the damaged part is removed. In a further development of the invention, detection means for the rope path and/or rope position, which determine the rope path covered or the position of the rope portion monitored for changes can be associated with the aforesaid detection means. The named detections means for the rope path and/or rope position can in particular detect a rope winch position which is present when the rope portion to be examined for change is just in the region of the corresponding detection device and is actually being monitored for changes, it is then possible in the evaluation device to calculate back from the named rope winch position which rope portion is damaged or worn.

In accordance with a further advantageous aspect of the present invention, alternatively or additionally to the named magnetically inductive monitoring of an embedded indicator section, a lengthening of the fiber rope can also be monitored and used for determining the discard state. The monitoring of the lengthening of the fiber rope starts from the consideration that an increasing wear of or damage to the fiber rope or the approaching toward the discard state is accompanied by a lengthening of the fiber rope with respect to its original state so that the monitoring of the lengthening of the fiber rope can be used as an indicator for the discard state. The detection device can for this purpose have determination means for determining the lengthening of the fiber rope, wherein the evaluation unit compares the determined lengthening with a permitted maximum lengthening. As soon as the lengthening exceeds a predefined measure, the discard state can be indicated.

Various procedures can be followed in this respect in the determination of the lengthening. In a first operating mode, the lengthening of the rope or rope portion substantially fully loaded can in particular be determined and monitored. Alternatively or additionally, in a second operating mode, the lengthening of the fiber rope can be examined portion-wise as to whether and to what extent predefined portions of the fiber rope lengthen.

In accordance with an advantageous embodiment of the invention, the determination means for determining the lengthening can have a position sensor for detecting the position of a predefined rope portion as well as a rope winch position sensor for detecting the winch position adopted on the traveling to the predefined rope position. The named position sensor can, for example, detect when an upper switch-off point for the load hook is reached and/or when a signaler applied to the rope, for example in the form of a mark, reaches a predefined site along the rope path. The rope winch position sensor detects the rope winch position present at this moment or on the reaching of the named position so that the evaluation unit can determine the rope lengthening from a change in the winch position adopted. If the winch position deviates too far from a desired position on reaching the predefined position of the predefined rope point, the discard state can be assumed or a discard signal can be output.

Alternatively or additionally, the fiber rope can be provided with a plurality of signalers distributed over its length, for example in the form of marks, transponders, signal reflectors or the like, and can thus be divided into a plurality of length portions. The determination means for determining the rope lengthening determine the distance of two respective signalers from which the evaluation unit can determine the length of the corresponding rope portions and can monitor it for changes. If lengthening phenomena take place in one or more rope portions which, individually or viewed in sum, go beyond a respective limit value for the permitted lengthening, the evaluation unit can output a discard signal.

In a further development of the invention, the named detection device can in this respect be configured such that a measuring device, for example an electronic measuring device, detects the passing or occurrence of the named signaler at a specific point along the rope path and measures the length distance up to the next signaler with a preferably constant rope speed. The rope length can hereby be split or divided into any desired number of measurement points and into any desired rope portions so that the course of stretching of the rope can be determined over the total rope length and it can be evaluated in the evaluation device in which rope section the limit value was reached and the rope has to be discarded or, if possible, has to be shortened by the discard region, i.e. the overstretched rope region.

The examination for lengthening is advantageously carried out under predefined conditions, in particular a predefined rope load, for example by attaching a test load, to eliminate any variance of the test results due to varying conditions.

In accordance with an advantageous further development of the invention, the load spectrum acting on the rope can also be used for the determination of the discard state of the fiber rope, in particular the tensile load acting on the rope and the bending cycles acting on the rope. A load spectrum counter can be provided for this purpose which detects at least the tensile rope stress and the number of bending cycles as the load spectrum acting on the fiber rope. The determination and evaluation of the named measured data is possible via corresponding determination means or detection means or sensors whose measured data are processed and evaluated in the evaluation device. A load sensor can in particular detect the ongoing strain of the rope via the operating time of the rope. A rotary encoder on the drum of the rope winch can determine the rope length which is strained to determine the bending cycles. The load data and the data on the rope path and on the bending cycles can be linked to one another in the evaluation device to determine a load spectrum which can be compared with a predefined permitted maximum load spectrum. If the number of the maximum permitted load spectrum is reached, the evaluation unit can output a corresponding discard signal.

It is generally possible to make use of different analytical approaches in the calculatory determination of the load spectra acting on the rope. In this respect, the consideration forms the starting point of drawing a conclusion on different degrees of damage on the basis of a calculated accumulation of damage in different load spectra and to store them in the control system. With a specific presetting of load changes it is then hereby possible to make a conclusion by calculation on the rope damage hereby arising, wherein a limit value can be fixed which allows an estimate of the discard state.

For example, a counting process can be used in the evaluation of the load spectra which occur, wherein the amplitude of the loads which occur can, for example, be presented via their sum frequency. Since in the normal case the fiber rope is not only subject to an ever-recurring equal load with a constant amplitude, but is also subject to a load which changes in amount, the load spectrum resulting in practice can, for example, be divided or stepped in individual rectangular spectra with a respective constant load and a partial load cycle criterion. For example, in accordance with the method known per se of linear damage accumulation, a partial damage can now be calculated for every partial spectrum in that the partial load cycle criterion is divided by the maximum load cycle criterion which can be tolerated. The partial damage of all partial spectra which thus results can be summed and be used as an indication of the total damage of the fiber rope. This approach of linear damage accumulation can also be modified in various manners in a manner likewise known per se, for example such that partial spectra whose load amplitudes are below the long-term strength limit are not taken into account or are only taken into account in a limited manner.

In a further development of the invention, the monitoring of the aforesaid changes in the fiber rope, in particular the magnetic change of an indicator section, the change in the rope lengthening and/or the change in the rope diameter can take place by a comparison of the correspondingly detected or determined parameters with previously detected or determined parameters. The corresponding reference values for the corresponding parameters, in particular the magnetic conductivity or property of the indicator section, the original rope length or the rope cross-sectional area can in particular take place in a reference detection mode with a new or still unimpaired fiber rope, for example in that the previously described procedures are worked through using a test weight on the putting into operation of the crane and the parameters determined in this process are stored in a reference value memory. In the further operation of the crane or lifting gear, the named parameters are then monitored continuously or cyclically and are compared with the initially stored reference values for them. If one or more of the named parameter shows a deviation with respect to the corresponding reference value which exceeds a permitted amount of deviation, the evaluation device can provide a discard signal. Alternatively or additionally, the named evaluation device can also provide the discard signal when admittedly none of the named parameters individually exceeds its permitted change value or deviation value, but the parameters show too great a deviation from the sum of the reference values when viewed in sum. If, for example, all determined parameters reach 90% of the permitted deviation from the reference value, each value would still be permitted viewed individually; nevertheless, the discard state can be indicated since not only one parameter, but rather all parameters, have almost reached their permitted change limits.

BRIEF DESCRIPTION OF THE DRAWINGS

The invention will be explained in more detail in the following with respect to a preferred embodiment and to associated drawings. There are shown in the drawings.

DETAILED DESCRIPTION

Figure 1:
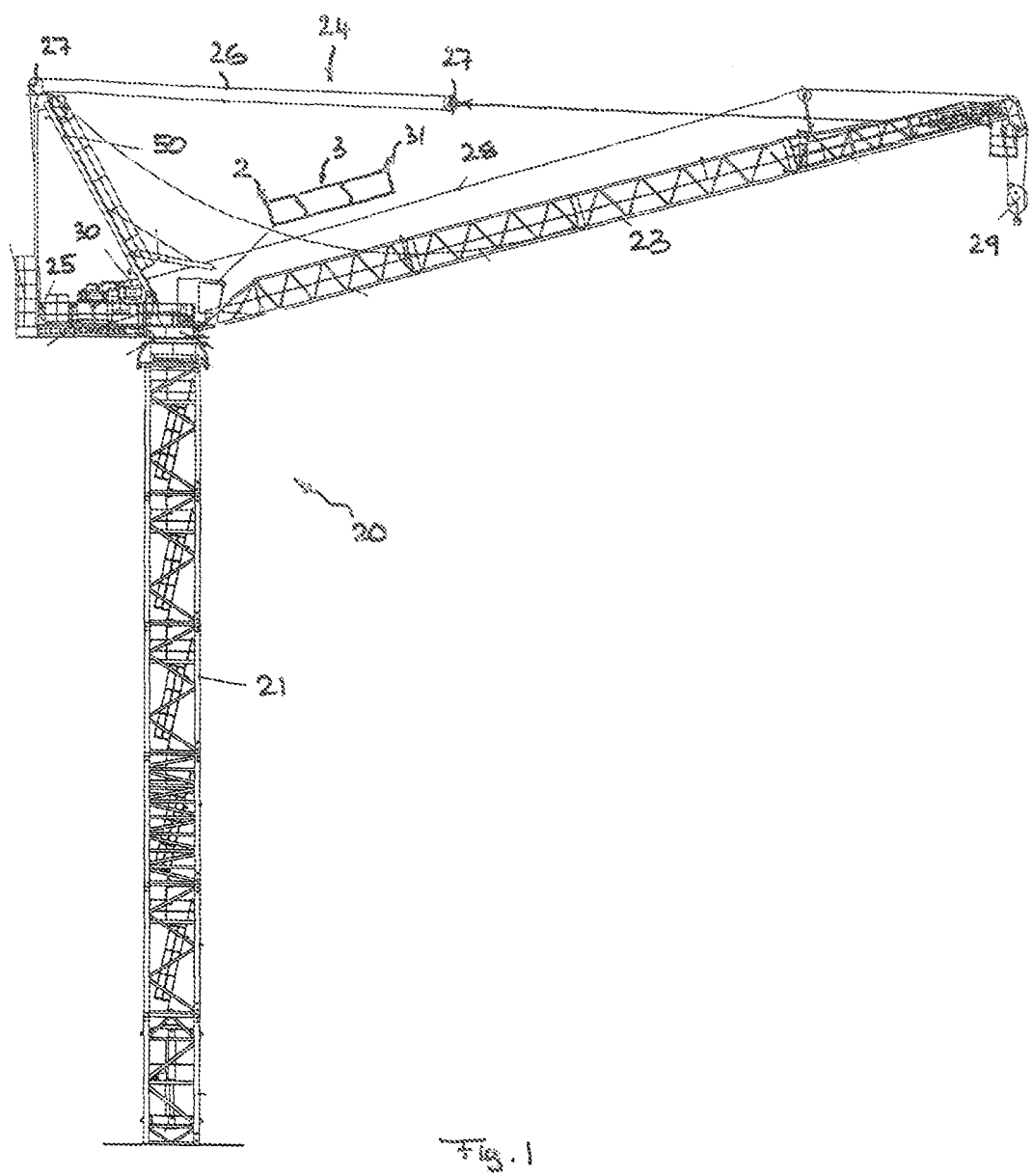
FIG. 1 is a schematic representation of lifting gear in accordance with the invention in the form of a revolving tower crane in accordance with an advantageous embodiment of the invention whose hoist rope and/or whose guy ropes for the luffable boom can be configured as fiber ropes.

FIG. 1 shows by way of example for lifting gear in accordance with an advantageous embodiment of the invention a crane in the form of a revolving tower crane 20 which revolves at the top and whose tower 21 is supported on a carriage or on a stationary base. A boom 23 is pivotably connected to the tower 21 in a luffable manner about a horizontal axis in a manner known per se and is guyed via a guying rope arrangement 24. The named guying rope arrangement 24 can be varied in its length via a guying rope winch 25 so that the working angle of the boom 23 can be changed. For this purpose, a guy rope 26 runs onto the named guy rope winch 25. The guy rope 26 or the guying rope arrangement 24 is guided at a pivot point at the boom 23 close to the tip of the boom 23 via, for example, pulley blocks 27 at the shown guy brace 50 or a tower tip.

Figure 2:
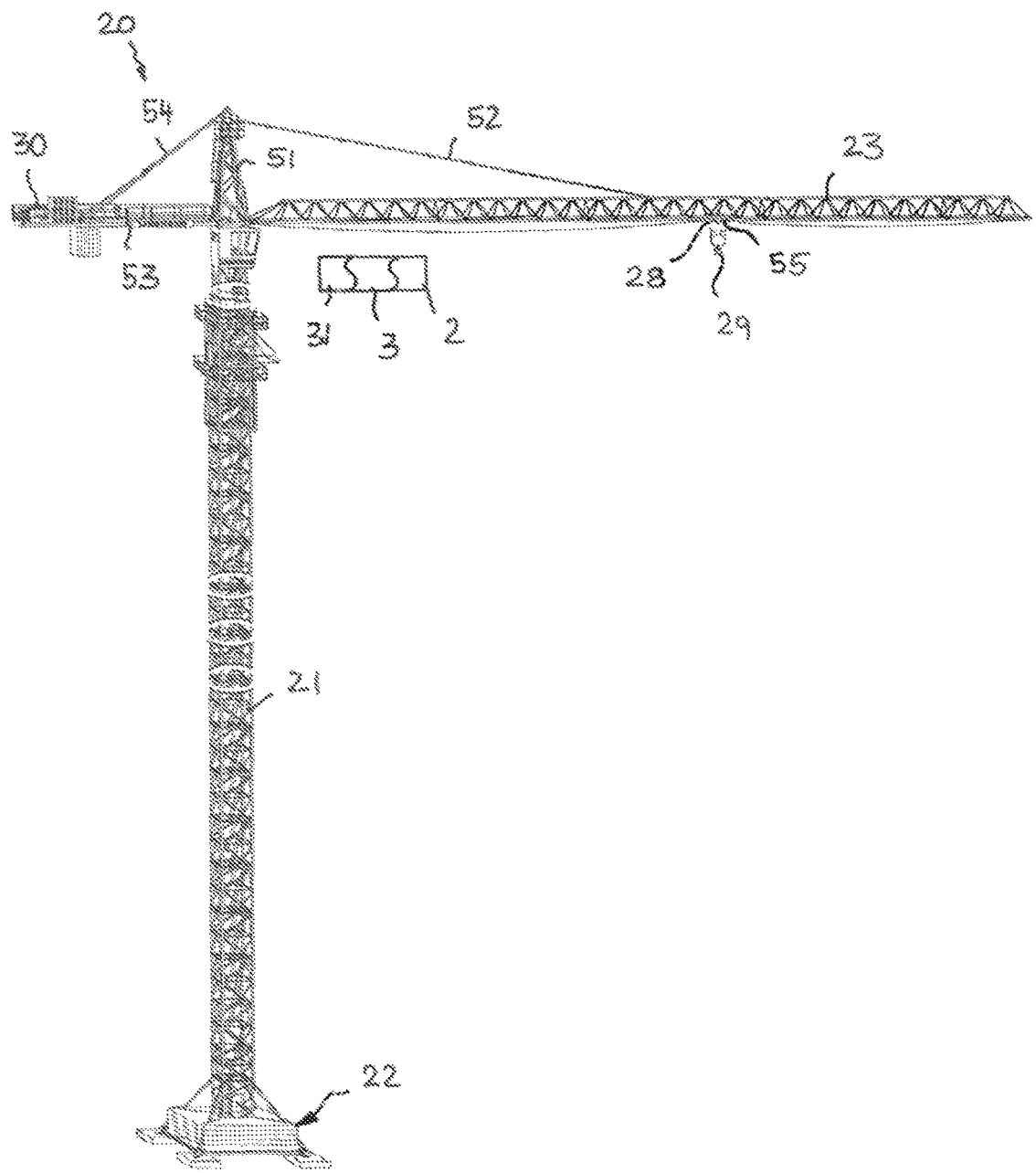
FIG. 2 is a schematic representation of a revolving tower crane similar to FIG. 1 in a modified embodiment in accordance with which the hoist rope does not run over the tip of a luffable boom, but rather over a trolley movable along the boom.

As FIG. 2 shows, the revolving tower crane 20 can naturally also be provided with a trolley boom. The revolving tower crane 20 which likewise revolves at the top and whose tower 21 is anchored to the base 22 provided with ballast has a boom 23 which is horizontal in the operating position, which is in particular aligned horizontally and which is guyed via guying tensioning means, for example in the form of guying bars 52, at the tower tip 51, wherein the counter-boom 53 provided with ballast is also guyed via guying tensioning means 54 at the named tower tip 51. A trolley 55 is movably supported at the aforesaid boom 23, wherein the named trolley 55 can be moved by means of a trolley rope, for example, which can be guided at the boom tip via pulley blocks.

The revolving tower crane furthermore comprises a hoist rope 28 which in the drawn embodiment in accordance with FIG. 1 can be let down from the tip of the boom via pulley blocks at the boom tip and is there connected to a crane hook 29 or, in the embodiment in accordance with FIG. 2, can run off via the said movable trolley 55 and the pulley blocks provided there and can be connected to the crane hook 29. The named hoist rope 27 in both cases runs onto a hoist winch 30 which, like the guy rope winch 25 of the embodiment in accordance with FIG. 1, is arranged in the region of the ballast frame or in another support part at the counter-boom 53.

The named hoist rope 28 and/or the guy rope 26 can in this respect be configured as a fiber rope which can comprise synthetic fibers such as aramid fibers or an aramid/carbon fiber mixture.

To be able to monitor or detect parameters of the named fiber rope relevant to the discard state, a detection device 2 is provided which can be arranged at the crane and which, together with an evaluation device 3 which evaluates the detected parameters, can be connected to or integrated in the electronic crane control unit 31.

Figure 3:
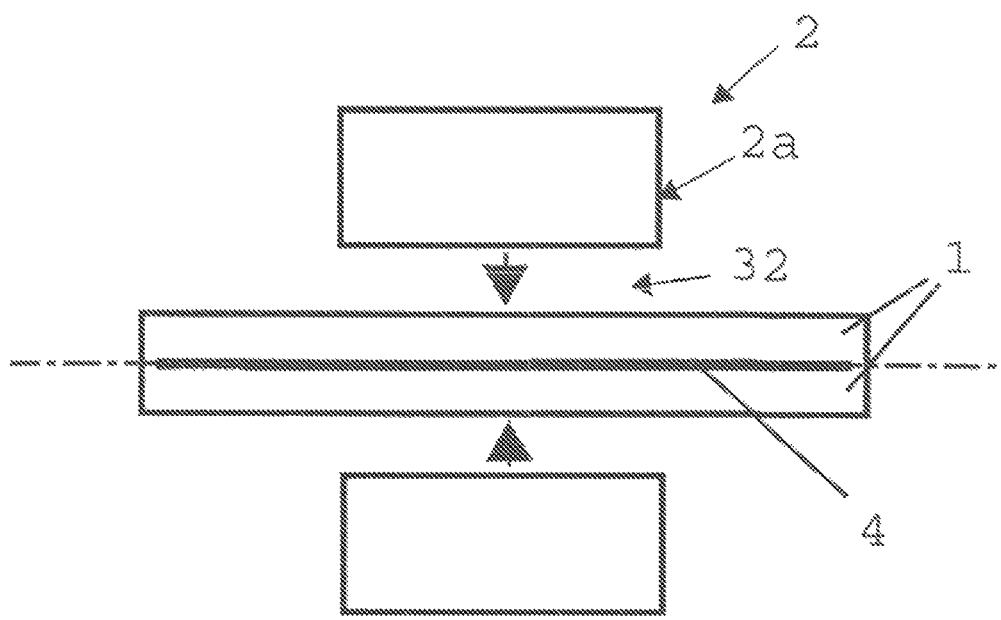
FIG. 3 is a schematic representation of the detection means for the magnetically inductive monitoring of changes of an indicator section embedded into the fiber rope.
Figure 4:
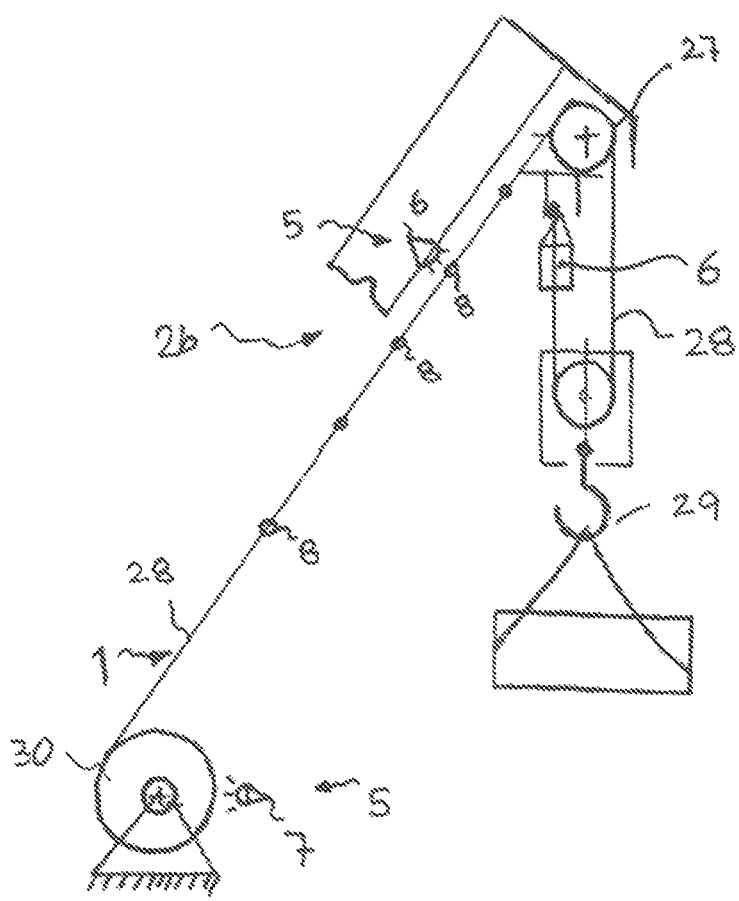
FIG. 4 is a schematic representation of the detection means for detecting a lengthening of the fiber rope.
Figure 5:
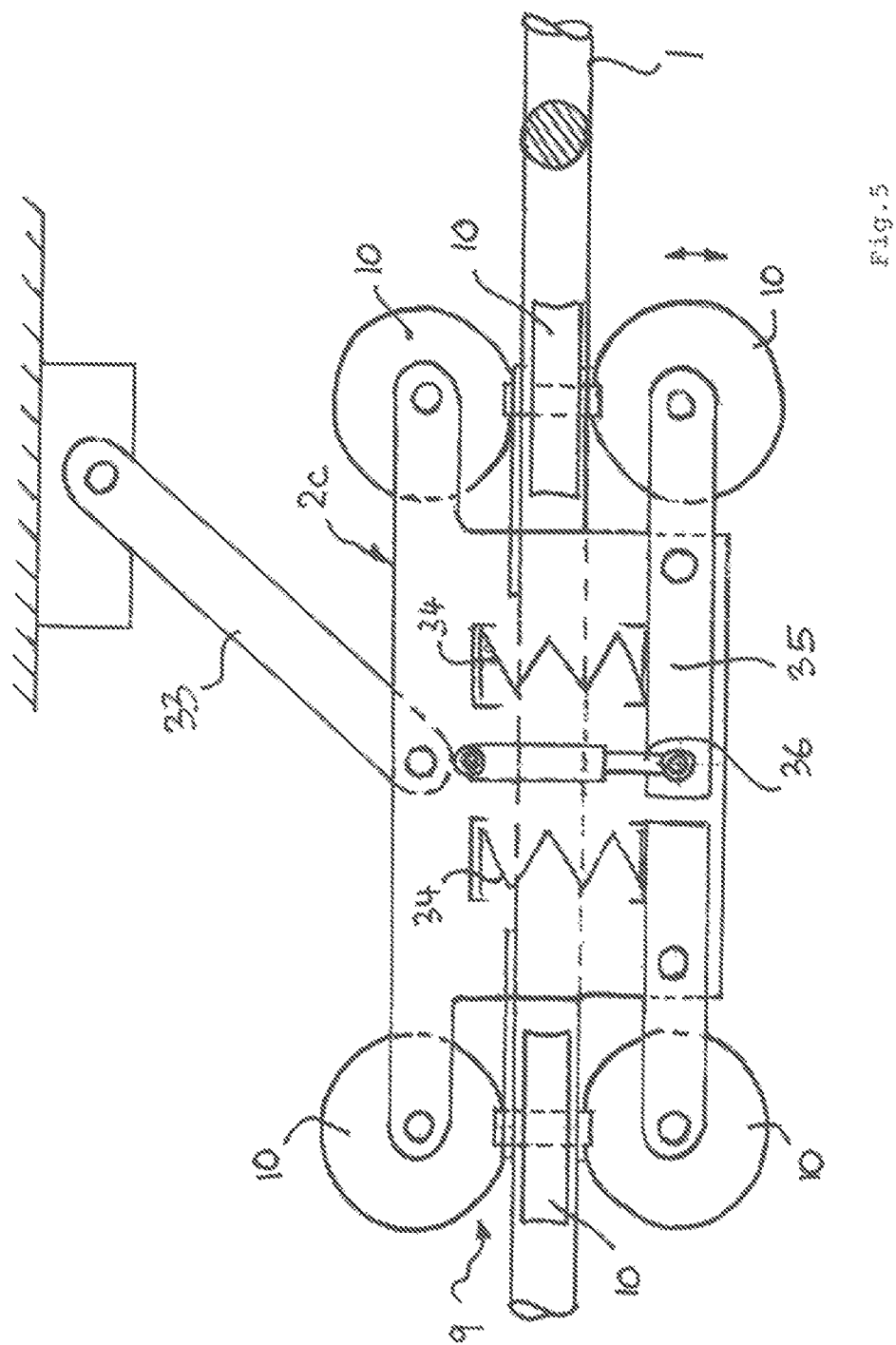
FIG. 5 is a schematic representation of the detection means for detecting cross-sectional changes in the fiber rope.

As FIGS. 3-5 show, the named detection device 2 in this respect advantageously comprises different detection means to detect different parameters of the fiber rope 1 in different manners. In accordance with FIG. 3, the named detection device 2 can comprise magnetically operating detection means 2a which detect changes in an indicator section 4 which is embedded in the fiber rope 1 and which is configured as magnetically conductive or as influencing a magnetic field or as magnetizable and which can also be incorporated in the rope. For example, the named indicator section 4 can be arranged in the core in the strand or therebetween, wherein the named indicator section 4 can itself generally have any desired cross-sectional shapes and can advantageously be provided with a round cross-section. The named indicator section 4 can in particular be formed from a metallic continuous material such as a wire, wherein the indicator section 4 is advantageously constituted such that it is configured as less resistant with respect to rope loads, stretching, tension, bending, torsion, temperature and other relevant properties than the fibers of the fiber rope 1 or the fiber rope 1 itself so that the indicator section 4 fails before a failure of the fiber rope 1 occurs.

The named magnetic detection means 2a, which can influence a magnetic field sensor, for example, detect the changes in a magnetic field which acts on the named indicator section 4 or is generated by it. A break of the named indicator section 4 in this respect in particular results in changes in the named magnetic field 32 so that a conclusion can be drawn from the detection of the corresponding characteristic magnetic field change on a break of the indicator section 4 and from this in turn on the discard state of the fiber rope 1.

To be able to determine in which region of the fiber rope 1 the break of the indicator section 4 occurs, a rope path measurement can be associated with the detection device 2 or its magnetic detection means 2a and is effected by suitable rope path detection means 5, for example in that a rotational position sensor 7 associated with the rope winch, of FIG. 4, indicates the rotational position of the rope winch or in that position sensors 6, of FIG. 4, detect marked rope sections at a specific position at which the named magnetic detection means 2a report the defect site. The evaluation device 3 can determine exactly where the defect site was determined from the known position of the detection means 2a The required time period for discarding the fiber rope 1 is advantageously displayed, e.g. on the monitor of the crane control, on the basis of a still remaining residual service life of the high-strength fiber rope. If discard does not take place in the set time, the crane control unit 31 can automatically deactivate the crane for safety reasons.

As FIG. 4 shows, the aforesaid detection device 2 furthermore advantageously comprises detection means 2b for determining a lengthening of the fiber rope 1 occurring gradually in operation. In this respect, a specific position can be traveled to by the fiber rope 1, for example by a direct traveling to the upper switch-off point at which the load hook 29 has reached the highest possible position and which can be detected, for example, by a limit switch or by another position sensor 6. If the named position sensor 6 reports to the detection means 2h that the predefined rope position has been reached, the position of the rope winch is detected or determined by a rope winch position sensor 7. This measurement is first carried out on the first putting into operation of the crane. If a different rope winch position is adopted on later measurements when the predefined desired position is traveled to, the deviation in the rope drum position for the traveling to the same rope point is a measure for the lengthening of the fiber rope 1 which has occurred. The test cycles are preferably carried out using a predefined load at the load hook 29, for example using a known test load, so that no varying conditions influence the measuring precision.

In this method of the detection of the rope lengthening by measuring the increasing drum revolution up to the switch-off point, it must be noted that it is an average value of the rope lengthening. The rope stretching is dependent on the load and on the duration of the load. If a load is moved, e.g. "raise", the rope region which is not coiled onto the rope drum always has the full and longest strain until the load is removed again. The rope tension, and thus also the stretch load, continuously reduces in the rope region which is coiled onto the drum. The stretching of the rope outside the rope drum will thus extend approximately constant and always have the maximum strain. In the rope which is coiled onto the drum, the tensile load which is present reduces continuously since the rope load on tension reduces to approximately zero after some winds. The limit of the permitted lengthening can be determined in this method using a stretch distribution factor with respect to the total rope length to obtain a sufficient security for the time of the discard state of the fiber rope 1.

A further method of rope lengthening testing with respect to the discard state is based on signalers 8 or indicators which output signals actively or inactively. These indicators are fixedly integrated at approximately equal intervals in the rope. A measuring device, e.g. an electrical/electronic measuring device, for example in the form of a position sensor 6, detects the point of the indicator and measures the length distance up to the next indicator at a constant rope speed. The rope length can thus be divided over any desired measurement points and an evaluation is obtained using this method on the stretch extent of the rope over the total rope length and it is recognized using a measuring device in which rope region the limit value was reached and the rope is discarded or, where possible, is shortened by the discard region, i.e. the overstretched rope region.

The measuring device is set on the first putting into operation. A predefined lifting motion is carried out using the mode e.g. "rope test". In this respect, travel is carried out at a constant lifting speed from the lowest position of the load hook 29 into the highest position. In this procedure, the distance lengths of the named plurality of indicators 8 are detected and stored. At a later point in time, the procedure is repeated after a corresponding period of use and the length difference from the first measurement is calculated and displayed. The measuring device forwards the values to the crane control and to the memory module; a forwarding by remote data transfer is possible by the crane control or the crane operator is advised of the state of the rope on the crane monitor. When unpermitted stretch is reached, a safety mode becomes active and if not observed, the warning and the switching off of the system takes place after a permitted remaining period of use. For safety reasons, the system can no longer be put into operation if it has been taken out of operation. The stopping reason is also displayed on the monitor and can also be accessed by remote data transmission.

As FIG. 5 shows, the detection device 4 can advantageously also comprise detection means 2c for determining changes in the rope cross-section and/or in the transverse compressive strength of the fiber rope 1. The named detection means 2c for this purpose advantageously detect the rope diameter or the transverse compressive stiffness in at least two planes which can advantageously stand perpendicular to one another in order also to be able to determine the rope cross-sectional area from the plurality of rope diameters with changes of the rope cross-sectional shape not harmful per se. This has the background that high-strength fiber ropes 1 tend to ovalizing in cross-section under transverse loads such as at the pulley blocks 27 or at the rope winches 25 or 30, said ovalizing per se not yet bringing along any impairment of the rope strength. It does become critical, however, when the rope cross-sectional area reduces.

In the embodiment in accordance with FIG. 5, the rope diameters are mechanically sampled for this purpose in mutually perpendicular planes using clamping means pairs in the form of rope rollers 10 which are pressed against the surface of the fiber rope 1 from oppositely disposed sides so that the clearance between the clamping means in the form of the rope rollers 10 is a measure for the corresponding rope diameter.

As FIG. 5 shows, the detection means 2c are supported overall transversely to the longitudinal direction of the rope so that transverse movements of the fiber rope 1 have no effects on the measurement result. In the embodiment drawn, the total apparatus is in this respect suspended transversely movably via a pivot frame or a lever pivot connection 33, of FIG. 5.

The measuring device advantageously has at least two rollers in the front region and two rollers in the rear in one plane of which the respective lower roller easily clamps the rope 1 via springs 34 and thus detects the rope diameter. One of these lower sprung rollers 10 has a rotary axle and a lever 35 via which the measured rope diameter is transferred to a position sensor 36 and is thus evaluated. The measuring unit has further lateral guide rollers for the rope so that the measuring unit is guided over the rope and possible rope vibrations have no effect on the measured values. The measuring unit is pivotally suspended via a lever at the steel construction of the crane to compensate movements. The rope measurement advantageously takes place offset by 90° over at least two planes so that the rope diameter is tested over four regions. A further offset arrangement, e.g. for six regions, is possible. The measurement over 2-4-6, etc. regions can be provided constructionally in a measurement unit or by an arrangement of a plurality of measurement units.

A further possibility arises by use of optical test units which recognize and evaluate a rope diameter change with respect to the circumference. On an exceeding or falling below of the permitted diameter deviation, a warning signal is given and the position is stored via the drum speed sensor 7.

In order also to be able precisely to determine the transverse compressive stiffness using the previously shown measurement unit in accordance with FIG. 5, in a further development of the invention, an adjustment apparatus can be associated with the clamping jaws or clamping rollers 10 and a variable and/or sufficiently high transverse force load of the rope can be generated using it, i.e. the rollers 10 can be pressed transversely against the rope with sufficient force. In this respect, the respective applied transverse force can advantageously be measured by a suitable force measuring device. The adopted deformation of the rope 1 is measured by the position sensor 36, wherein the initially explained changes of adjustment force and/or transverse deformation can be effected in one or more measurement cycles.

If the warning signal is not observed, the warning and switching off of the system advantageously takes place after a permitted residual time of use. For safety reasons, the system can no longer be put into operation if it has been taken out of operation. The stopping reason is also displayed on the monitor and can also be accessed by remote data transmission.

Furthermore the named detection device 2 can advantageously also comprise detection means 2d for detecting the load spectrum acting on the respective fiber rope 1, wherein here at least the tensile load acting on the rope and the number of bending cycles, but advantageously also other parameters influencing the long-term strength such as multilayer coiling, environmental influences, temperature, transverse strains and others, can advantageously be detected here.

To determine the named parameters, the named detection means 24 comprise corresponding sensors whose signals occur in the named evaluation unit 3. A load sensor can in particular detect the ongoing load via the operating time of the rope. Furthermore, a rotary encoder on the respective winch drum can measure the rope length which is strained. In sum, a load spectrum can be determined from this, for example in the form of a Wöhler curve, which can be compared with a predefined maximum load spectrum for the fiber rope 1. If the number of the maximum permitted load spectrum, that is a specific number of bending cycles under the influence of a specific load and/or specific load peaks, is reached, a warning and/or a time in which the rope change has to take place is/are carried out.

We claim:

1. An apparatus for recognizing a replacement state of a high-strength fiber rope having a load hook for use with a lifting gear, in particular a crane, comprising:
    a detection device for detecting at least one rope parameter comprising:
        a detector for detecting a lengthening of the high-strength fiber rope, wherein the detector comprises:
            a position sensor for detecting a predefined rope point at a predefined position in terms of the load hook being at a predefined load hook position, comprising an upper switch-off point for the load hook, a rope winch position sensor for detecting a winch position when the high-strength fiber rope reaches the predefined tope point at the predefined position;
    an evaluation device for evaluating the at least one rope parameter and for providing a discard signal in dependence on the at least one rope parameter evaluation, wherein the evaluation device is configured to monitor a change in the winch position between a first test run when a test load is attached to the load hook, and a second test run when the test load is attached to the load hook, and provide the discard signal when the change in the winch position exceeds a predefined amount during the second test run.

2. The apparatus of claim 1, wherein the evaluation device evaluates the at least one, rope parameter when the high-strength fiber rope is used to lift a test load.

3. The apparatus of claim 2, wherein the test load is lifted at a constant speed.

4. The apparatus of claim 1, wherein the position sensor is an electronic position sensor.

5. The apparatus of claim 1, further comprising a crane control unit configured to deactivate a crane comprising the lifting gear after the evaluation device provides the discard signal.

6. The apparatus of claim 1, wherein the change in the winch position is a change in a revolution of a winch drum.

7. An apparatus for recognizing a replacement state of a high-strength fiber rope having a load hook for use with a lifting gear, in particular a crane, comprising:
    a detection device for detecting at least one rope parameter comprising:
        a plurality of signalers distributed over a length of the high-strength fiber rope, wherein the plurality of signalers are configured for detecting a lengthening of the high-strength fiber rope;
        a determiner for determining a distance between two of the plurality of signalers, wherein the determiner comprises two position sensors for determining the positions of the two of the plurality of signalers; and
    an evaluation device for evaluating at least one rope parameter and for providing a discard signal in dependence on the at least one rope parameter evaluation, wherein the evaluation device is configured to evaluate a change in the distance between the two of the plurality of signalers between a first test run when a test load is attached to the load hook, and a second test run when the test load is attached to the load hook, and provide the discard signal when the change in the distance between the two of the plurality of signals exceeds a predefined distance change during the second test run.

8. The apparatus of claim 7, wherein the plurality of signalers comprise at least one of marks, transponders, or signal reflectors.

9. The apparatus of claim 7, wherein the plurality of signalers are distributed at equal intervals over the length of the high-strength fiber rope.

10. The apparatus of claim 7, wherein the plurality of signalers actively output a signal.

11. The apparatus of claim 7, wherein the distance between the two of the plurality of signalers is stored in a memory module.

12. The apparatus of claim 7, wherein the evaluation device evaluates the at least one rope parameter when the high-strength fiber rope is used to lift a test load.

13. The apparatus of claim 12, wherein the test load is lifted at a constant speed.

* * * * *